(12) United States Patent
Hempel et al.

(10) Patent No.: US 8,233,967 B2
(45) Date of Patent: Jul. 31, 2012

(54) METHOD FOR MARKING AND VISUALIZING AN IMPLANT BY WAY OF AN X-RAY PHASE-CONTRAST TOMOGRAPHY EXAMINATION AND AN IMPLANT

(75) Inventors: Eckhard Hempel, Fürth (DE); Martin Hoheisel, Erlangen (DE); Stefan Popescu, Erlangen (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 849 days.

(21) Appl. No.: 12/222,505

(22) Filed: Aug. 11, 2008

(65) Prior Publication Data

US 2009/0052614 A1   Feb. 26, 2009

(30) Foreign Application Priority Data

Aug. 14, 2007   (DE) .................. 10 2007 038 381

(51) Int. Cl.
*G01N 23/02* (2006.01)

(52) U.S. Cl. ............ 600/431; 600/433; 600/425; 378/4; 378/8; 378/62; 382/131

(58) Field of Classification Search .................. None
See application file for complete search history.

(56) References Cited

U.S. PATENT DOCUMENTS

2005/0244337 A1*  11/2005  Wang et al. ............... 424/9.36
2007/0183584 A1*   8/2007  Baumann et al. .......... 378/145
2007/0189449 A1    8/2007  Baumann et al.

FOREIGN PATENT DOCUMENTS

DE  102006017291    8/2007
EP  1447046         8/2004

OTHER PUBLICATIONS

Philipp Bernhardt, Lothar Bätz, Ernst-Peter Rührnschopf, Martin Hoheisei; Spatial Frequency-Dependent Signal-to-Noise Ratio as a Generalized Measure of Image Quality. Bernhardt et al.; Medical Imaging 2005: Physics of Medical Imaging, edited by Michael J. Flynn, Proceedings of SPIE vol. 5745, pp. 407-418. (SPIE, Bellingham, WA, 2005). Others; 2005.
German Office Action dated Feb. 29, 2008.

\* cited by examiner

*Primary Examiner* — Long V Le
*Assistant Examiner* — Farshad Negarestan
(74) *Attorney, Agent, or Firm* — Harness, Dickey & Pierce, P.L.C.

(57) ABSTRACT

A method is disclosed for marking and visualizing an implant by use of an x-ray phase-contrast tomography examination. Further, an implant is also disclosed. In at least one embodiment, implants are used with specific characteristics which are as unambiguous as possible with regard to the phase shift generated by the implants in a phase-contrast tomography examination. In at least one embodiment, these specific characteristics can include the typical self-generated specific phase shift, typical differences in the specific phase-shift values, or typical spatial structures of materials with well-defined phase-shift values.

17 Claims, 2 Drawing Sheets

METHOD FOR MARKING AND VISUALIZING AN IMPLANT BY WAY OF AN X-RAY PHASE-CONTRAST TOMOGRAPHY EXAMINATION AND AN IMPLANT

PRIORITY STATEMENT

The present application hereby claims priority under 35 U.S.C. §119 on German patent application number DE 10 2007 038 381.0 filed Aug. 14, 2007, the entire contents of which is hereby incorporated herein by reference.

FIELD

Embodiments of the invention generally relate to a method for marking and visualizing an implant in a patient by way of an x-ray phase-contrast tomography examination (=x-ray phase-contrast CT). In at least one embodiment, at least one portion of the patient is scanned by x-ray radiation which passes through a first x-ray absorption grating prior to reaching the patient, and at least the phase shifts of the x-ray radiation in this portion caused locally are also made detectable by using a second phase grating downstream of the patient in the emission direction. Further, the spatial distribution of these shifts is measured and reconstructed, wherein an average specific phase-shift value is assigned to each spatial unit. Furthermore, embodiments of the invention also generally relate to an implant designed for the abovementioned method.

BACKGROUND

It is generally known to use stents (=vascular prostheses), placed using fluoroscopy, in angiography. For this purpose, the stents have to be very conspicuous so that they are precisely deployed at the desired location. However, stents are often not very conspicuous because it is necessary to use the lowest x-ray doses possible, especially in more time-consuming procedures. The same situation arises when using guide wires which have to be very thin and, as a consequence, they too are often not visible enough when irradiated. Similar problems also occur when using catheters, or when using implants in general.

Previously the x-ray spectrum in examinations and treatments controlled by fluoroscopy was optimized to the effect that the stents and guide wires, composed of different metal alloys, had the largest possible contrast with respect to the surrounding tissue. However, the contrast, and hence the visibility, often remained unsatisfactory, especially in the case of low x-ray doses.

In order to nevertheless ensure the visibility of stents, markers composed of a heavy metal, for example gold, are affixed to the ends of the stents. These are more visible in conditions prevailing in fluoroscopy. However, only individual points are highlighted. The visibility of the precise progression of stents, catheters or guide wires over their entire length is not improved. Furthermore, markers do not allow monitoring of the correct deployment of a stent.

SUMMARY

In at least one embodiment of the invention, a method is disclosed for marking and visualization which allows reliable recognition of implants in the body of a patient when using a low dose. Likewise, a correspondingly designed implant should be found.

The inventor has recognized that it is possible to image removable or permanent implants, in particular stents (=vascular prostheses), guide wires or catheters, using an x-ray method based on phase-contrast and to identify them unambiguously. With the previously used fluoroscopy, which is based on x-ray absorption, the aim was to achieve highest possible absorption. For this purpose, it was necessary preferably to use materials which contain elements with a high atomic number Z. Such materials are either very expensive, or the human body displays a low tolerance toward them. In order to generate a contrast which is as unambiguous as possible in a phase-contrast x-ray CT, high absorption is immaterial; the refractive index of the material through which the radiation passes is all that matters.

Thus, according to at least one embodiment of the invention it is now also possible to use materials which have the lowest possible density. It is advantageous to manufacture catheters and stents from plastics which have favorable elastic properties and which are biocompatible. These materials have very little or no contrast to the surrounding tissue in absorption x-ray examinations. Previously such materials with low absorptivity had been out of the question. However, plastics with a low density are readily available because many plastics have a lower density than soft tissue. Such materials have a lower refractive index for x-ray radiation in the diagnostic energy range. For this reason they have a highly visible contrast when a phase-contrast method is used.

In another embodiment of the invention, implants, in particular stents, catheters or guide wires, having a conventional construction can be used, although they are coated with a lower-density plastic, which in turn is conspicuous in phase-contrast imaging.

It is also possible to use inhomogeneously structured plastics as an alternative to the low-density plastics described above. By way of example, microscopically small gas bubbles which generate a typical phase contrast could have been introduced.

It is also possible to use plastics with a higher density instead of using lower-density plastics, it being crucial that the density of the plastic differs from the density of the respectively surrounding soft tissue.

In a further embodiment of the invention, it is possible that the plastic is made from materials which are known to be biodegradable in the body, in particular for the coating of the implants (=stents, catheters and guide wires). The advantage of using such materials is that they can be optimized for the desired phase-contrast imaging at the time of the intervention and the subsequent check-up, but they need not remain in the body of the patient in the long term.

Furthermore, it is proposed to use specially encoded structures in these implants. These structures are intended to generate unmistakable phase patterns. Hence, a stent or catheter for example is produced such that it contains a spatially periodic structure which excites defined, constant phase oscillations at the x-ray energy used.

According to the basic idea of at least one embodiment of the invention, the inventors particularly propose a method for marking and visualizing an implant in a patient by means of an x-ray phase-contrast CT, wherein at least one portion of a patient is scanned by x-ray radiation which passes through a first x-ray absorption grating prior to reaching the patient, and wherein at least the phase shifts of the x-ray radiation in this portion caused locally are also made detectable by using a second phase grating downstream of the patient in the emission direction, and the spatial distribution of these shifts is measured and reconstructed, wherein an average specific phase-shift value is assigned to each spatial unit. The implant located in the patient is now intended to comprise a material which generates in a spatial unit an average specific phase-shift value which differs significantly from the average specific phase-shift values of human tissue.

In terms of at least one embodiment of the invention, spatial units are understood to be two-dimensional areas of a slice image, that is to say one or more pixels, or three-dimensional regions of a volume data record, that is to say one or more connected voxels, depending on the reconstruction method. Accordingly, it is now possible to seek areas with a specified average specific phase-shift value, which is only caused by a particular material of the implant.

It is preferable to select for the implant a material whose average specific phase-shift value lies in the range between 45° and 135° and is preferably 90°.

According to another variant of the idea according to at least one embodiment of the invention, a method for visualizing an implant in a patient by means of an x-ray phase-contrast CT is also proposed, wherein at least one portion of the patient is scanned by x-ray radiation which passes through a first x-ray absorption grating prior to reaching the patient, and wherein at least the phase shifts of the x-ray radiation in this portion caused locally are also made detectable by using a second phase grating downstream of the patient in the emission direction, and the spatial distribution of these shifts is measured and reconstructed to form volume data records, that is to say 3D views or slice image views, wherein an average specific phase-shift value is assigned to each spatial unit. According to at least one embodiment of the invention, the implant located in the patient has at least two adjacently arranged materials which each generate an average specific phase-shift value in a spatial unit, the difference in these values being defined and known, and in which adjacent differences in the phase-shift value are furthermore sought in the generated volume data records, and an implant is considered to be recognized when these predefined differences in the phase-shift value occur.

Thus it is not a single phase-shift value that is sought in this case, but rather at least one difference in values between adjacent spatial units.

In this context it is advantageous if the difference in the phase-shift value of the at least two materials of the implant is significantly greater than the maximum difference in phase-shift value of any two types of human tissue. This absolutely ensures that no mix-ups with anatomical or other structures can occur.

In a further modification of the idea according to at least one embodiment of the invention, the inventors also propose a method for visualizing an implant in a patient by means of an x-ray phase-contrast CT, wherein at least one portion of the patient is scanned by x-ray radiation which passes through a first x-ray absorption grating prior to reaching the patient, and wherein at least the phase shifts of the x-ray radiation in this portion caused locally are also made detectable by using a second phase grating downstream of the patient in the emission direction, and the spatial distribution of these shifts is measured and reconstructed to form volume data records, wherein an average specific phase-shift value is assigned to each spatial unit. According to at least one embodiment of the invention, the implant located in the patient is at least in part composed of a first material and a second material, wherein the second material is distributed in the first material in particulate form, and the two materials respectively generate an average specific phase-shift value in a spatial unit, the difference in these values being known. Adjacent differences in the phase-shift value are now sought in the generated volume data records, and an implant is considered to be recognized when these predefined differences in the phase-shift value occur.

With regard to the abovementioned variants of at least one embodiment of the method, it is proposed that a cluster of $n^3$ voxels or $n^2$ pixels is considered to be a spatial unit, wherein n is a whole number between 1 and 3 inclusive. As a result of an increasing number n, statistical variation which cannot be suppressed can be compensated for to a large extent.

It is also advantageous if at least one material of the implant, preferably a coating, is designed such that in time it is absorbed in the body of a patient.

Furthermore, the implant can have a specific material structure which allows an unambiguous characterization or an unambiguous identification. The material structure of the implant can preferably be designed in the form of a bar code.

By way of example, a stent, a guide wire or a catheter can be used as an implant.

In accordance with at least one embodiment of the method described above, the inventors additionally propose an implant for use in a patient, wherein the implant comprises at least one material which generates in a spatial unit in a phase-contrast CT an average specific phase-shift value which differs significantly from the average specific phase-shift values of human tissue.

Preferably, it is possible to select the at least one material such that its average specific phase-shift value lies in the range between 45° and 135° and is preferably 90°.

Alternatively, an implant for use in a patient is proposed, in which at least two materials are provided, are arranged adjacent to one another and respectively generate an average specific phase-shift value in a spatial unit, the difference in these values being known.

This difference in the phase-shift value of the at least two materials of the implant should be significantly greater than the maximum difference in phase-shift value of any two types of human tissue.

Furthermore, an implant for use in a patient which is at least in part composed of a first material and a second material is proposed, wherein the second material is distributed in the first material in particulate form, and the two materials respectively generate an average specific phase-shift value in a spatial unit, the difference in these values being known.

In this definition of the implants, a cluster of $n^3$ voxels or $n^2$ pixels can be preferably considered to be a spatial unit, wherein n is a whole number between 1 and 3 inclusive.

Furthermore, it is advantageous if at least one material of the implant is designed to be bio-absorbable in the body of a patient.

In addition, a specific material structure which allows unambiguous characterization and/or identification can be provided. Preferably, the material structure can be designed in the form of a bar code.

By way of example, the implant can be a stent, a guide wire, or a catheter.

BRIEF DESCRIPTION OF THE DRAWINGS

In the following, the invention will be described in more detail on the basis of example embodiments with the aid of the figures, with only features required to understand the invention being shown. In this context, the following reference symbols are used: 1: x-ray phase-contrast CT system; 2: first x-ray tube; 2.1: first grating of the first tube detector system; 3: first detector; 3.1: second grating of the first tube detector system; 4: second x-ray tube; 4.1: first grating of the second tube detector system; 5: second detector; 5.1: second grating of the second tube detector system; 6: gantry housing; 7:

patient; 8: patient couch; 9: system axis; 10: control and computational unit; 11: memory of the control and computational unit; 20: implant; 21: catheter; 21.1: tip of the catheter; 21.2: spiral wire in the catheter; 21.3: casing of the catheter; 22: stent; M1, M2, M3: materials; $\Delta\phi_{V1}, \Delta\phi_{V2}, \Delta\phi_{V3}$: specific phase-shift values; $|\Delta\phi_{V1}-\Delta\phi_{V2}|$: difference in the phase-shift value; $Prg_1-Prg_x$: computer programs.

Figure 1:
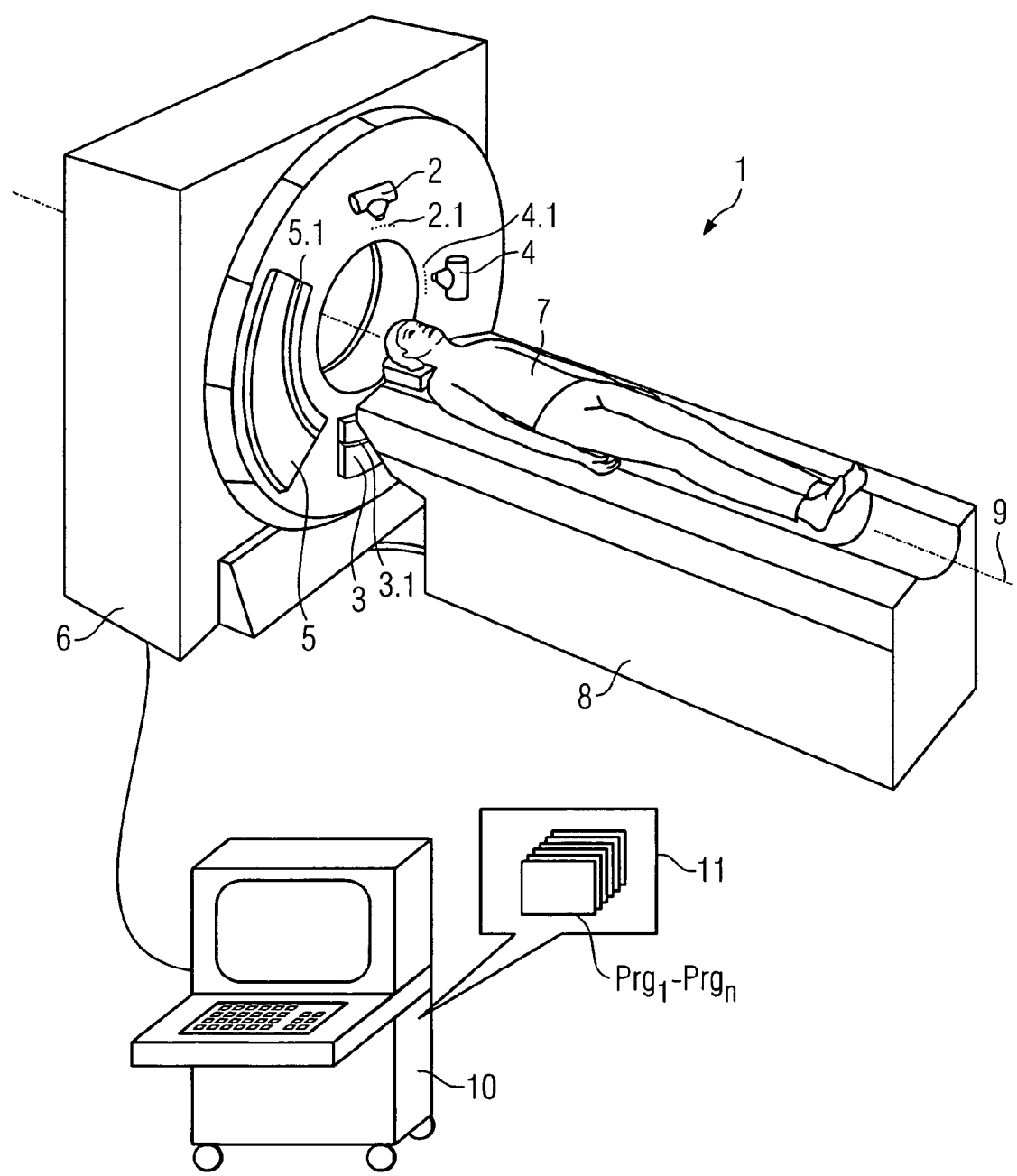
Figure 2:
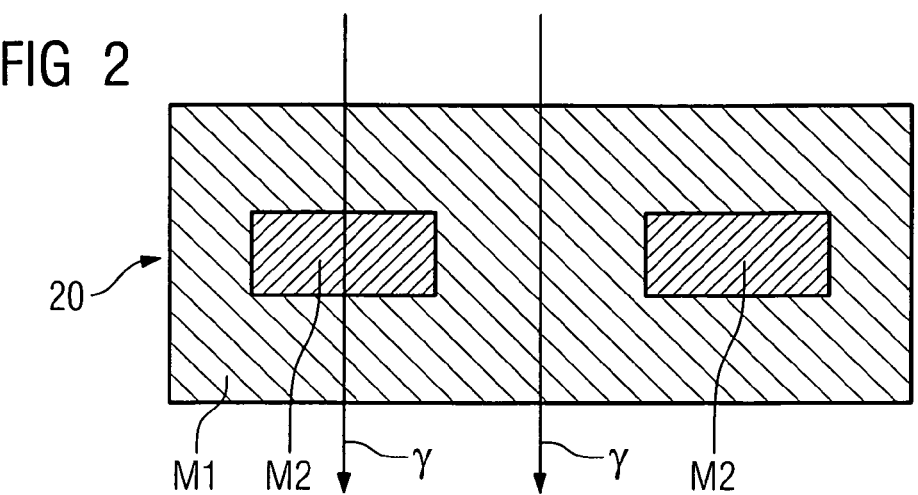
Figure 3:
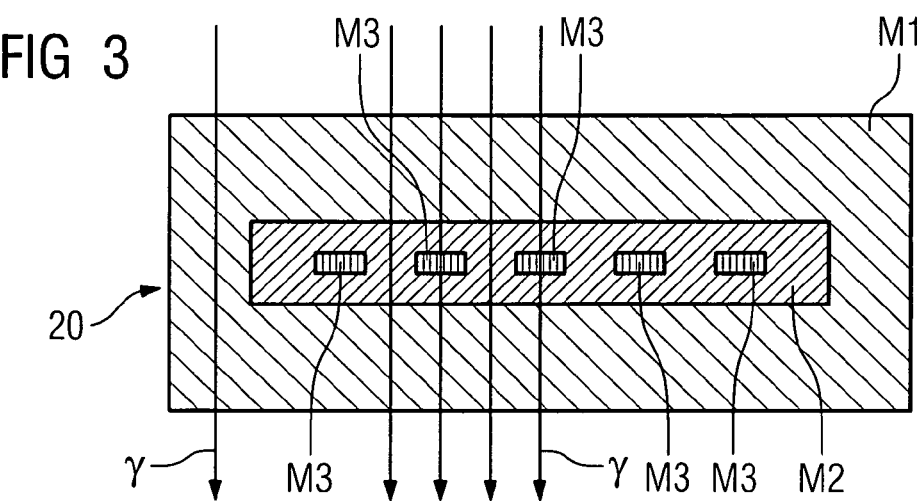
Figure 4:
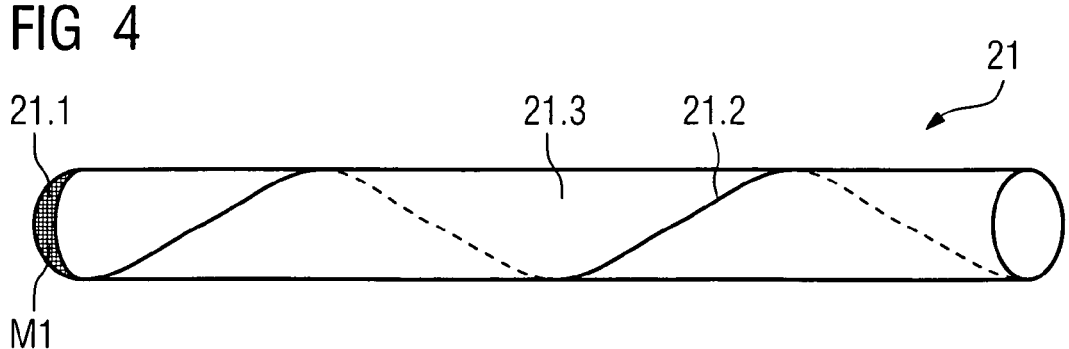
Figure 5:
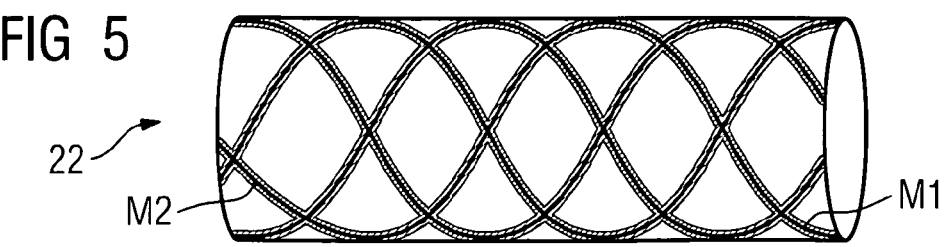

In detail,

FIG. 1 shows an x-ray phase-contrast CT system for carrying out the method according to an embodiment of the invention, FIG. 2 shows a cross section through a structure of an implant according to an embodiment of the invention composed of different materials, FIG. 3 shows a cross section through a structure of an implant according to an embodiment of the invention composed of three different materials, FIG. 4 shows a side view of a catheter with a tip according to an embodiment of the invention, and FIG. 5 shows a side view of a stent designed according to an embodiment of the invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an x-ray phase-contrast CT system 1 with a gantry housing 6, in which a revolvable gantry is located and on which at least a first emitter-detector system and optionally further emitter-detector systems can be arranged.

Two emitter-detector systems are shown in the present illustration. In this case, the first emitter-detector system comprises a first x-ray tube 2 with an x-ray absorption grating 2.1 arranged in front of the patient for generating quasi-coherent x-ray radiation. Furthermore, the first emitter-detector system has a detector 3 with an upstream x-ray grating 3.1 opposite the x-ray tube 2 for generating interference and thus making the phase shift of the x-ray radiation "visible"; the x-ray radiation differs depending on the observed beam passing through the patient 7. The second emitter-detector system shown here likewise comprises an x-ray tube 4 with an absorption grating 4.1 and a detector 5 with an upstream phase grating 5.1; it co-rotates with the first emitter-detector system on the gantry about the system axis 9 and makes a measurement offset by 90° to the first emitter-detector system possible.

During the scan, the patient 7 is pushed through the measurement field on a patient couch 8 along the system axis 9 while the emitter-detector systems on the gantry rotate about the system axis 9. This results in a helical scan. Alternatively, a sequential scanning process can also be carried out; in this case the patient 7 is pushed through the measuring zone incrementally, with a circular scan being carried out after each feed.

The basic mode of operation and particular embodiments of such phase-contrast CT systems has already been described explicitly in a number of previous applications from the applicant in the field of phase-contrast CT, and in other publications in the prior art.

The CT system 1 is controlled by a control and computational unit 10, with this control and computational unit 10 maintaining the work programs with their program code in a main memory 11 for operation. This main memory also contains, inter alia, programs $Prg_1$ to $Prg_n$ which emulate the method according to an embodiment of the invention described above and can execute it during operation.

If a patient 7 whose body contains an implant designed according to an embodiment of the invention is scanned by such a phase-contrast CT system or by a similar system, this implant can be located easily due to its specific characteristics with regard to its specific phase-shift value $\Delta\phi_V$, and, if desired, it can be shown separately in views in a highlighted manner. Different peculiarities can be used in this case as a specific characteristic with regard to generating and detecting phase-shifts.

By way of example, the implant can have a defined specific phase-shift value $\Delta\phi_V$ which otherwise does not occur in the body, in °/mm for example. After the scan, the system can now seek occurrences of these specific phase-shift values in a targeted manner, and all accumulations of pixels with this phase-shift value or very similar phase-shift values can be sought and can be shown in a view, highlighted optically if appropriate.

Another variant of a specific characteristic of an implant which is to be found in a phase-contrast CT can consist of the fact that the implant has a specified combination of two or more different specific phase-shift values $\Delta\phi_V$. Thus, the occurrence of adjacent or specifically spaced-apart spatial units which have a predetermined difference in phase-shift values are sought in the phase-contrast CT image data determined by a scan.

FIG. 2 illustrates an example of an implant 20 with two well-defined materials M1 and M2 in a cross section. The two materials in each case have specific phase-shift values $\Delta\phi_{V1}$ and $\Delta\phi_{V2}$; however, these can also be similar to those of materials occurring in the body. In this case it is important that the difference in magnitude of these specific phase-shift values $\Delta\phi_{V1}$ and $\Delta\phi_{V2}$, that is to say the difference in the phase-shift value $|\Delta\phi_{V1}-\Delta\phi_{V2}|$, does not occur for the individual materials or that at least the spatial structure, having this difference in the phase-shift value which can be detected, does not occur for the individual materials. In this manner, such a structure, and hence the implant itself, can easily be detected, and, in particular, it can also be detected by the automated algorithms of an image processing or image filtering unit.

By way of example, each spatial unit with a specified phase-shift value $\Delta\phi_{V1}$ and comprising one or more pixels or voxels can be examined with regard to the presence of another spatial unit having another specified phase-shift value $\Delta\phi_{V2}$ at a specified distance. It is also possible to directly seek the presence of specified differences in the phase-shift value $|\Delta\phi_{V1}-\Delta\phi_{V2}|$ between adjacent spatial units, if applicable at a specified distance apart. If the structures are additionally arranged at a clearly defined, recurrent intervals, then the detection can also be carried out by simple frequency filters.

FIG. 3 shows a variant of an implant 20 with three different materials M1 to M3—shaded differently—and correspondingly different specific phase-shift values $\Delta\phi_{V1}$, $\Delta\phi_{V2}$, and $\Delta\phi_{V3}$. Here, the material M3 is embedded in material M2 which in turn is embedded in material M1. In addition, the material M3 has a structural distribution which leads to a typical spatial oscillation of the phase-shift values and which can easily be detected in a phase-contrast CT view using a frequency filter. If such detection is made, then surrounding material M1, being the outer structure of the implant, can be displayed in an optically highlighted manner. In addition, it is possible to unambiguously characterize or individually identify the implant by the number of materials or the spatial arrangement of the materials.

FIG. 4 shows a catheter 21 in which the tip of the catheter 21.1 is embodied using a material M1 with a defined specific phase-shift value. Furthermore, a spiral insert 21.2 of a material M2 is arranged around the catheter or within the catheter casing 21.3 such that a defined phase gradient is created, which can be recognized more easily in an overview image. The materials and dimensions of the casing 21.3 and of the spiral insert 21.2 can in this case be chosen such that the desired phase gradient is created in the phase-contrast CT at the x-ray energy used. Alternatively, the tip 21.1 of the catheter 21 can also, for example, be composed of a material which contains microscopic particles of another material, which in turn create a defined phase shift.

Finally, FIG. 5 shows a further example embodiment of a stent 22, with the aid of which visibility and recognizability in the phase-contrast CT is improved. In this case, the shown structures of materials M1 and M2, from which, according to an embodiment of the invention, the stent is constructed, provide a predefined and known difference of the phase-shift value and a predefined structure which can be sought in a phase contrast view in a targeted manner. By way of example, according to the invention it is possible that the outer material M1 comprises a body-absorbent material, which decomposes after the use of the stent 22 and, if appropriate, with medicinal effects in the immediate surroundings. A frame of the material M2 remains and creates the mechanical properties of the stent 22.

It is self-evident that the abovementioned features of embodiments of the invention can be used not only in the respectively specified combinations, but also in other combinations or on their own, without departing from the scope of the invention.

Furthermore, reference is made to the fact that a phase-contrast CT system is understood to mean both CT systems with a conventional gantry, similar to FIG. 1, and C-arm systems. In this case, it is only important that the computed tomography system can determine phase shifts of x-ray radiation passing through a patient and resolve specific phase-shift values in slices or volume data records. For completeness, it should also be mentioned that the method according to embodiments of the invention described above can be carried out both using differential methods for determining the phase contrast, in which only phase shifts in the range from 0 to n can be recognized, and also by using integrating methods, in which the actual total phase shift when passing through an object is determined.

Overall, at least one embodiment of the invention thus proposes using implants with specific characteristics which are as unambiguous as possible with regard to the phase shift they generate in a phase-contrast CT and it being possible that these specific characteristics occur due to the typical self-generated specific phase shift, typical differences in the specific phase shift or typical spatial structures made of materials with well-defined phase-shift values.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing an implant in a patient by using an x-ray phase-contrast tomography examination, the method comprising:
scanning at least one portion of a patient by x-ray radiation which passes through a first x-ray absorption grating prior to reaching the patient;
detecting at least phase-shifts of the x-ray radiation in the at least one portion caused locally by using a second phase grating downstream of the patient in an emission direction;
measuring and reconstructing a spatial distribution of the detected phase shifts to generate volume data records;
assigning an average specific phase-shift value to each of a plurality of spatial units, wherein the implant located in the at least one portion of the patient includes at least two adjacently arranged materials, each of which generating an average specific phase-shift value per spatial unit, a difference in the generated average specific phase-shift values being defined and known;
checking for an occurrence of the known difference in the average specific phase-shift values in the generated volume data records; and
recognizing the implant when the known difference in the average specific phase-shift values is found to occur in the generated volume data records.

2. The method as claimed in claim 1, wherein the difference in the phase-shift value of the at least two materials of the implant is significantly greater than the maximum difference in phase-shift value of any two types of human tissues.

3. The method as claimed in claim 1, wherein a cluster of $n^3$ voxels or $n^2$ pixels is considered to be a spatial unit among the plurality of spatial units, wherein n is a whole number between 1 and 3 inclusive.

4. The method as claimed in claim 1, wherein at least one of the materials of the implant is designed to be bio-absorbable in the body of the patient.

5. The method as claimed in claim 1, wherein the implant has a specific material structure which allows unambiguous characterization of the implant.

6. The method as claimed in claim 1, wherein the implant has a specific material structure which allows unambiguous identification of the implant.

7. The method as claimed in claim 1, wherein a stent is used as the implant.

8. The method as claimed in claim 1, wherein a guide wire is used as the implant.

9. The method as claimed in claim 1, wherein a catheter is used as the implant.

10. A method for visualizing an implant in a patient by using an x-ray phase-contrast tomography examination, the method comprising:
scanning at least one portion of a patient by x-ray radiation which passes through a first x-ray absorption grating prior to reaching the patient;
detecting at least phase-shifts of the x-ray radiation in the at least one portion caused locally by using a second phase grating downstream of the patient in an emission direction;
measuring and reconstructing a spatial distribution of the detected phase shifts to generate volume data records;
assigning an average specific phase-shift value to each of a plurality of spatial units, wherein the implant located in the at least one portion of the patient includes at least in part a first material and a second material, wherein the second material is distributed in the first material in particulate form;
respectively generating, using the two materials, an average specific phase-shift value per spatial unit, a difference in the respectively generated average specific phase-shift values being known;
checking for an occurrence of the known difference in the average specific phase-shift values in the generated volume data records; and
recognizing the implant when the known difference in the average specific phase-shift values is found to occur.

11. The method as claimed in claim 10, wherein a cluster of $n^3$ voxels or $n^2$ pixels is considered to be a spatial unit among the plurality of spatial units, wherein n is a whole number between 1 and 3 inclusive.

12. The method as claimed in claim 10, wherein at least one of the materials of the implant is designed to be bio-absorbable in the body of the patient.

13. The method as claimed in claim 10, wherein the implant has a specific material structure which allows unambiguous characterization of the implant.

14. The method as claimed in claim 10, wherein the implant has a specific material structure which allows unambiguous identification of the implant.

15. The method as claimed in claim 10, wherein a stent is used as the implant.

16. The method as claimed in claim 10, wherein a guide wire is used as the implant.

17. The method as claimed in claim 10, wherein a catheter is used as the implant.

* * * * *